United States Patent
King

(10) Patent No.: US 7,214,764 B2
(45) Date of Patent: May 8, 2007

(54) FREE RADICAL QUENCH PROCESS FOR IRRADIATED ULTRAHIGH MOLECULAR WEIGHT POLYETHYLENE

(75) Inventor: Richard King, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/795,755

(22) Filed: Mar. 8, 2004

(65) Prior Publication Data

US 2004/0266903 A1    Dec. 30, 2004

Related U.S. Application Data

(63) Continuation-in-part of application No. 10/609,749, filed on Jun. 30, 2003, now abandoned.

(51) Int. Cl.
*C08F 6/00* (2006.01)

(52) U.S. Cl. ............... 528/480; 264/488; 522/153; 623/21; 623/22; 623/23; 623/26

(58) Field of Classification Search ............... 264/488; 522/153; 528/480; 623/22.21, 23.26
See application file for complete search history.

(56) References Cited

U.S. PATENT DOCUMENTS

| | | | |
|---|---|---|---|
| 5,288,818 | A | 2/1994 | Livingston, Jr. et al. |
| 5,414,049 | A | 5/1995 | Sun et al. |
| 5,489,303 | A | 2/1996 | Sasaki et al. |
| 5,593,719 | A | 1/1997 | Dearnaley et al. |
| 5,594,055 | A | 1/1997 | Young |
| 5,721,334 | A | 2/1998 | Burstein et al. |
| 5,827,904 | A | 10/1998 | Hahn |
| 5,844,027 | A | 12/1998 | Burdick et al. |
| 5,879,400 | A * | 3/1999 | Merrill et al. ............ 623/22.11 |
| 6,017,975 | A | 1/2000 | Saum et al. |
| 6,174,934 | B1 | 1/2001 | Sun et al. |
| 6,228,900 | B1 | 5/2001 | Shen et al. |
| 6,242,507 | B1 | 6/2001 | Saum et al. |
| 6,277,390 | B1 | 8/2001 | Schaffner |
| 6,281,264 | B1 | 8/2001 | Salovey et al. |
| 6,316,158 | B1 | 11/2001 | Saum et al. |
| 6,329,465 | B1 * | 12/2001 | Takahashi et al. .......... 525/191 |
| 6,395,799 | B1 | 5/2002 | Johnson |
| 6,448,315 | B1 | 9/2002 | Lidgren et al. |
| 6,494,917 | B1 * | 12/2002 | McKellop et al. ........ 623/23.58 |
| 2002/0125614 | A1 | 9/2002 | King et al. |
| 2003/0125513 | A1 | 7/2003 | King |
| 2003/0149125 | A1 | 8/2003 | Muratoglu et al. |
| 2003/0193110 | A1 | 10/2003 | Yaritz et al. |
| 2003/0212161 | A1 | 11/2003 | McKellop et al. |
| 2004/0156879 | A1 | 8/2004 | Muratoglu et al. |
| 2004/0265165 | A1 | 12/2004 | King |

FOREIGN PATENT DOCUMENTS

| | | |
|---|---|---|
| EP | 0 047 171 A2 | 3/1982 |
| EP | 0 730 001 A1 | 9/1996 |
| EP | 0 805 178 A1 | 11/1997 |
| EP | 1493775 A1 | 1/2005 |
| JP | 60-252645 A | 12/1985 |
| WO | 97/29895 A1 | 8/1997 |
| WO | WO 99/52474 * | 10/1999 |
| WO | WO 00/49079 A1 | 8/2000 |
| WO | 02/26464 A1 | 4/2002 |
| WO | WO 3049930 * | 6/2003 |
| WO | 03/087217 A1 | 10/2003 |
| WO | WO 2004/064618 A2 | 8/2004 |

OTHER PUBLICATIONS

Barr et al., "EPR as a Quality Control Method for the Release of Cross-Linked Ultra High Molecular Weight Polyethylene," Bruker EPR Application Note (Feb. 28, 2003).
Oral et al. *Biomaterials*, 25(24), pp. 5515-5522 (2004).

* cited by examiner

*Primary Examiner*—Terressa Boykin
(74) *Attorney, Agent, or Firm*—Leydig, Voit & Mayer, Ltd.

(57) ABSTRACT

The invention provides a process for quenching free radicals present in irradiated ultrahigh molecular weight polyethylene comprising the steps of (a) providing a mass of irradiated ultrahigh molecular weight polyethylene, wherein the mass comprises free radicals, (b) immersing at least a portion of the mass of irradiated ultrahigh molecular weight polyethylene in a non-polar solvent having a temperature for a time and under conditions sufficient to quench a substantial portion of the free radicals contained therein, wherein the temperature of the non-polar solvent is maintained below the melting point of the ultrahigh molecular weight polyethylene, (c) removing the mass of irradiated ultrahigh molecular weight polyethylene from the non-polar solvent, and (d) removing any non-polar solvent from the mass of irradiated ultrahigh molecular weight polyethylene.

22 Claims, No Drawings

FREE RADICAL QUENCH PROCESS FOR IRRADIATED ULTRAHIGH MOLECULAR WEIGHT POLYETHYLENE

CROSS-REFERENCE TO RELATED PATENT APPLICATIONS

This patent application is a continuation-in-part of U.S. patent application Ser. No. 10/609,749, filed Jun. 30, 2003, now abandoned.

FIELD OF THE INVENTION

This invention pertains to a process for quenching free radicals present in irradiated ultrahigh molecular weight polyethylene. The resulting polyethylene is particularly well suited for use in making orthopaedic implants or orthopaedic implant parts.

BACKGROUND OF THE INVENTION

Ultrahigh molecular weight polyethylene ("UHMWPE") is commonly used in making orthopaedic implants, such as artificial hip joints. In recent years, it has become increasingly apparent that tissue necrosis and osteolysis at the interface of the orthopaedic implant and the host bone are primary contributors to the long-term loosening failure of prosthetic joints. It is generally accepted by orthopaedic surgeons and biomaterials scientists that this tissue necrosis and osteolysis is due, at least in part, to the presence of microscopic particles of UHMWPE produced during the wear of the UHMWPE components. The reaction of the body to these particles includes inflammation and deterioration of the tissues, particularly the bone to which the orthopaedic implant is anchored. Eventually, the orthopaedic implant becomes painfully loose and must be revised.

In order to increase the useful life of orthopaedic implants having UHMWPE parts, several attempts have been made to increase the wear resistance of the UHMWPE, thereby decreasing the number of wear particles that can cause tissue necrosis and/or osteolysis. One method for increasing the wear resistance of UHMWPE utilizes exposure to high-energy radiation, such as gamma radiation, in an inert or reduced-pressure atmosphere to induce cross-linking between the polyethylene molecules. This cross-linking creates a three-dimensional network of polyethylene molecules within the polymer which renders it more resistant to wear, such as adhesive wear. However, the free radicals formed upon irradiation of UHMWPE can also participate in oxidation reactions which reduce the molecular weight of the polymer via chain scission, leading to degradation of mechanical properties, embrittlement, and a significant increase in wear rate. These free radicals are very long-lived (greater than eight years), so that oxidation can continue over a very long period of time resulting in as much as a 5-fold increase in the wear rate as a result of oxidation over a period of about 5 years. Therefore, the long term wear resistance of irradiated UHMWPE, and the useful life of an orthopaedic implant having irradiated UHMWPE parts, substantially depends upon reducing the number of free radicals present in the UHMWPE before it is exposed to an oxidizing environment, such as air or the oxygen-rich in vivo environment.

There are several processes that have been developed to effectively and efficiently reduce the number of free radicals present in irradiated UHMWPE, all of which have met with varying degrees of success. For example, U.S. Pat. No. 5,414,049 discloses a process in which an irradiated formed implant of UHMWPE is heated to a temperature between 37° C. and the melting point of the UHMWPE in an oxygen-reduced, non-reactive atmosphere for a length of time sufficient to reduce the number of free radicals present in the UHMWPE. The disclosed process typically requires at least forty-eight hours (and up to 144 hours) to substantially reduce the number of free radicals. While the process does reduce the number of free radicals contained within the UHMWPE, there can be significant costs associated with heating the irradiated formed implant of UHMWPE for such an extended period of time.

A need therefore exists for a process for effectively and rapidly quenching the free radicals present in irradiated UHMWPE. The invention provides such a process. These and other advantages of the invention, as well as additional inventive features, will be apparent from the description of the invention provided herein.

BRIEF SUMMARY OF THE INVENTION

The invention provides a process for quenching free radicals present in irradiated ultrahigh molecular weight polyethylene comprising the steps of (a) providing a mass of irradiated ultrahigh molecular weight polyethylene, wherein the ultrahigh molecular weight polyethylene has a weight average molecular weight of about 400,000 atomic mass units or more, and the mass comprises free radicals, (b) immersing at least a portion of the mass of irradiated ultrahigh molecular weight polyethylene in a non-polar solvent having a temperature for a time and under conditions sufficient to quench a substantial portion of the free radicals contained therein, wherein the temperature of the non-polar solvent is maintained below the melting point of the ultrahigh molecular weight polyethylene, (c) removing the mass of irradiated ultrahigh molecular weight polyethylene from the non-polar solvent, and (d) removing any non-polar solvent from the mass of irradiated ultrahigh molecular weight polyethylene.

DETAILED DESCRIPTION OF THE INVENTION

The invention provides a process for quenching free radicals present in irradiated ultrahigh molecular weight polyethylene. The process comprises the steps of (a) providing a mass of irradiated ultrahigh molecular weight polyethylene, wherein the ultrahigh molecular weight polyethylene has a weight average molecular weight of about 400,000 atomic mass units or more, and the mass comprises free radicals, (b) immersing at least a portion of the mass of irradiated ultrahigh molecular weight polyethylene in a non-polar solvent having a temperature for a time and under conditions sufficient to quench a substantial portion of the free radicals contained therein, wherein the temperature of the non-polar solvent is maintained below the melting point of the ultrahigh molecular weight polyethylene, (c) removing the mass of irradiated ultrahigh molecular weight polyethylene from the non-polar solvent, and (d) removing any non-polar solvent from the mass of irradiated ultrahigh molecular weight polyethylene.

As utilized herein, the term "ultrahigh molecular weight polyethylene" refers to a polyethylene polymer having a weight average molecular weight of about 400,000 atomic mass units or more. Preferably, the ultrahigh molecular weight polyethylene has a weight average molecular weight of about 1,000,000 (e.g., about 2,000,000 or about 3,000, 000) atomic mass units or more. Typically, the weight average molecular weight of the ultrahigh molecular weight polyethylene is less than 10,000,000 atomic mass units (e.g., about 10,000,000 atomic mass units or less), more preferably about 6,000,000 atomic mass units or less.

The term "mass of irradiated ultrahigh molecular weight polyethylene" refers to a shaped article comprising ultrahigh molecular weight polyethylene which has been consolidated, such as by ram extrusion or compression molding of ultrahigh molecular weight polyethylene resin particles into rods, sheets, blocks, slabs, or the like. The mass of irradiated ultrahigh molecular weight polyethylene may be obtained or machined from commercially available ultrahigh molecular weight polyethylene, such as GUR 1050 ram extruded ultrahigh molecular weight polyethylene rods from PolyHi Solidur (Fort Wayne, Ind.). Preferably, the mass of ultrahigh molecular weight polyethylene does not contain stabilizers, antioxidants, or other chemical additives which may have potential adverse effects in medical applications.

Typically, the mass of irradiated ultrahigh molecular weight polyethylene is sized and shaped so that a medical implant or medical implant part can easily be machined therefrom. Alternatively, the mass of irradiated ultrahigh molecular weight polyethylene comprises a medical implant or medical implant part. Suitable medical implants or medical implant parts include, but are not limited to, the acetabular cup, the insert or liner of the acetabular cup, or trunnion bearings (e.g., between the modular head and the stem) of artificial hip joints, the tibial plateau, patellar button (patello-femoral articulation), and trunnion or other bearing components of artificial knee joints, the talar surface (tibiotalar articulation) and other bearing components of artificial ankle joints, the radio-numeral joint, ulno-humeral joint, and other bearing components of artificial elbow joints, the glenoro-humeral articulation and other bearing components of artificial shoulder joints, intervertebral disk replacements and facet joint replacements for the spine, temporo-mandibular joints (jaw), and finger joints.

The mass of irradiated ultrahigh molecular weight polyethylene can be irradiated using any suitable method. For example, the mass of ultrahigh molecular weight polyethylene can be irradiated by exposing the mass to a suitable amount of gamma, x-ray, or electron beam radiation. Preferably, the mass of ultrahigh molecular weight polyethylene is irradiated by exposing the mass to about 0.5 to about 10 Mrad (e.g., about 1.5 to about 6 Mrad) of gamma radiation using methods known in the art. While the mass of irradiated ultrahigh molecular weight polyethylene can be exposed to amounts of radiation falling outside of the aforementioned range, such amounts of radiation tend to produce ultrahigh molecular weight polyethylene with unsatisfactory properties. In particular, radiation doses of less than about 0.5 Mrad generally provide insufficient cross-linking of the ultrahigh molecular weight polyethylene to provide the desired increase in wear properties. Furthermore, while doses of greater than 10 Mrad may be used, the additional improvement in wear properties of the ultrahigh molecular weight polyethylene that is achieved generally is offset by the increased brittleness of the ultrahigh molecular weight polyethylene due to higher levels of cross-linking.

Preferably, the mass of ultrahigh molecular weight polyethylene is irradiated in an inert or reduced-pressure atmosphere. Irradiating the mass of ultrahigh molecular weight polyethylene in an inert (i.e., non-oxidizing) or reduced-pressure atmosphere reduces the effects of oxidation and chain scission reactions which can occur during irradiation in an oxidative atmosphere. Typically, the mass of ultrahigh molecular weight polyethylene is placed in an oxygen-impermeable package during the irradiation step. Suitable oxygen-impermeable packaging materials include, but are not limited to, aluminum, polyester coated metal foil (e.g., the Mylar® product available from DuPont Teijin Films), polyethylene terephthalate, and poly(ethylene vinyl alcohol). In order to further reduce the amount of oxidation which occurs during the irradiation of the mass of ultrahigh molecular weight polyethylene, the oxygen-impermeable packaging may be evacuated (e.g., the pressure within the packaging may be reduced below the ambient atmospheric pressure) and/or flushed with an inert gas (e.g., nitrogen, argon, helium, or mixtures thereof) after the mass of ultrahigh molecular weight polyethylene has been placed therein.

The mass of irradiated ultrahigh molecular weight polyethylene can be immersed in any suitable non-polar solvent. Preferably, the non-polar solvent is capable of swelling the immersed portion of the ultrahigh molecular weight polyethylene. The non-polar solvent is preferably selected from the group consisting of non-polar low molecular weight solvents having a molecular weight of less than 700 and non-polar biocompatible lipids. Low molecular weight solvents suitable for use in the invention include, but are not limited to, aliphatic hydrocarbons (e.g., heptane, octane, nonane, and decane), decalin, octanol, cineole, and mixtures thereof. Alternatively, the low molecular weight solvent can be selected from the group consisting of aromatic solvents having a boiling point that is higher than the melting point of UHMWPE, such as cumene and xylene (e.g., o-xylene). Suitable non-polar biocompatible lipids include, but are not limited to, fatty acids (e.g., stearic acid), glycerides (e.g., triglycerides such as tristearin), polyisoprenoids (e.g., squalene), cholesterol, cholesterol derivatives (e.g., cholesterol esters such as cholesteryl stearate and cholesteryl palmitate), tocopherol derivatives (e.g., tocopherol esters such as tocopherol acetate), and mixtures thereof. Saturated hydrocarbons (e.g., squalane) are also suitable for quenching free radicals.

The temperature of the non-polar solvent can be maintained at any suitable temperature, provided the temperature is maintained below the melting point of the ultrahigh molecular weight polyethylene (e.g., a temperature of about 20° C. to about 130° C.). Preferably, the non-polar solvent is maintained at a temperature of about 100 to about 130° C., more preferably about 100 to about 120° C.

As noted above, the mass of irradiated ultrahigh molecular weight polyethylene should be immersed in the non-polar solvent for a time sufficient to swell the immersed ultrahigh molecular weight polyethylene and quench a substantial portion of the free radicals contained therein. It will be understood that the time required to swell the ultrahigh molecular weight polyethylene and quench a substantial portion of the free radicals contained therein will depend upon several factors, such as the size and shape of the mass, the surface area of the mass, the temperature of the non-polar solvent, the volume of the non-polar solvent, and the particular non-polar solvent being used. For example, the time required to swell and quench a substantial portion of the free radicals contained within a mass of irradiated ultrahigh molecular weight polyethylene using stearic acid may be different from the time required to swell and quench the free radicals within the same mass using decane. Furthermore, the time required to swell and quench a substantial portion of the free radicals contained within two similar masses of irradiated ultrahigh molecular weight polyethylene using the same non-polar solvent at the same temperature may differ if the relationship between the volume of the non-polar solvent and the surface area of each mass is different. Preferably, the mass of irradiated ultrahigh molecular weight polyethylene is immersed in the non-polar solvent for about 2 hours or more, more preferably about 3 hours or more (e.g., about 4 hours or more, about 5 hours or more, or about 6 hours or more). Generally, the mass of irradiated ultrahigh molecular weight polyethylene is immersed in the non-polar solvent for about 48 hours or less (e.g., about 40 hours or less), more typically about 36 hours or less (e.g., about 30 hours or less, about 24 hours or less, about 20 hours or less, or about 12 hours or less).

As utilized herein, the process of the invention quenches a substantial portion of the free radicals contained within the immersed portion of the mass of irradiated ultrahigh molecular weight polyethylene if about 50 percent or more (e.g., about 60 percent or more, or about 75 percent or more) of the free radicals present in the immersed portion of the mass are quenched. Preferably, the process of the invention quenches about 90 percent or more, more preferably about 95 percent or more, most preferably about 98 percent or more, of the free radicals present in the immersed portion of the mass of irradiated ultrahigh molecular weight polyethylene.

The presence and amount of free radicals present in the mass of irradiated ultrahigh molecular weight polyethylene can be measured using any suitable method. For instance, the presence and relative concentration of the free radicals present in the mass of irradiated ultrahigh molecular weight polyethylene can be determined by measuring the degree to which the irradiated ultrahigh molecular weight polyethylene oxidizes over time. The aging process can be accelerated by exposing the mass of irradiated ultrahigh molecular weight polyethylene to an atmosphere having an oxygen content that is higher than the atmospheric oxygen concentration, and the degree of oxidation can be measured using any suitable technique, such as Fourier-transform infrared spectroscopy (FT-IR). One suitable FTIR technique for determining the free radical concentration of irradiated ultrahigh molecular weight polyethylene is the method of Nagy & Li, A Fourier Transform Infrared Technique for the Evaluation of Polyethylene Bearing Materials, Transactions, 16th Annual Meeting, The Society for Biomaterials, 3:109 (1990). Preferably, the oxidation level of irradiated ultrahigh molecular weigh polyethylene quenched according to the process of the invention, when measured using the method of Nagy & Li, is about 8 carbonyl area/mm sample thickness or less (e.g., about 5 carbonyl area/mm sample thickness or less). Alternatively, the presence and relative concentration of free radicals present in the mass of irradiated ultrahigh molecular weight polyethylene can be directly measured using electron paramagnetic resonance (EPR) spectroscopy methods known in the art.

After the mass of irradiated ultrahigh molecular weight polyethylene is removed from the non-polar solvent, any residual non-polar solvent can be removed from the mass using any suitable method. For instance, when a non-polar low molecular weight solvent is used, the residual non-polar low molecular weight solvent can be removed from the mass by exposing the mass to a reduced pressure atmosphere. As utilized herein, the term "reduced pressure atmosphere" is used to refer to any environment having a pressure that is less than ambient atmospheric pressure. Alternatively, the residual non-polar low molecular weight solvent can be removed from the mass by exposing the mass to an elevated temperature that is well below the melting point of the ultrahigh molecular weight polyethylene (e.g., about 50° C., about 60° C., about 70° C., about 80° C., about 90° C., about 100° C. Preferably, the residual non-polar low molecular weight solvent is removed from the mass of irradiated ultrahigh molecular weight polyethylene by exposing the mass to a reduced pressure atmosphere and an elevated temperature. When an aromatic solvent is used to quench the free radicals in the UHMWPE, any solvent remaining in the UHMWPE can be extracted by immersing the UHMWPE in a supercritical fluid (e.g., supercritical hexane, decane, or $CO_2$). Alternatively, when a non-polar solvent having a high boiling point (e.g., a triglyceride) is used, the residual non-polar solvent can be removed by extraction using a low molecular weight solvent, which low molecular weight solvent can be later removed by exposing the mass to a reduced pressure atmosphere and/or an elevated temperature.

In each of the aforementioned methods for removing the non-polar solvent, the mass of irradiated ultrahigh molecular weight polyethylene is preferably exposed to a reduced pressure atmosphere and/or elevated temperature for a period of time sufficient to remove substantially all of the residual non-polar solvent or extraction fluid from the mass. Substantially all of the residual non-polar solvent or extraction fluid is considered to be removed from the mass of irradiated ultrahigh molecular weight polyethylene when the amount of residual non-polar solvent or extraction fluid remaining in the mass is considered safe for implantation in a host (e.g., human). Generally, the ultrahigh molecular weight polyethylene is considered to be safe for implantation when the concentration of the residual solvent or extraction fluid is less than about 10,000 parts-per-millions (ppm) (e.g., less than about 7,500 ppm or less than about 5,000 ppm). It will be further understood that the concentration of residual solvent or extraction fluid considered safe will depend upon the identity of the particular solvent or extraction fluid used (e.g., the concentration of xylene considered safe for implantation may be different from the concentration of heptane considered safe for implantation). It will be further understood that the amount of time necessary to remove substantially all of the residual non-polar solvent or extraction fluid from the mass will depend upon several factors, such as the boiling point of the non-polar solvent or extraction fluid, the pressure of the atmosphere to which the mass is exposed, and the temperature of the atmosphere to which the mass is exposed.

Following removal of the residual non-polar solvent, the mass of irradiated ultrahigh molecular weight polyethylene can be formed into a medical implant or medical implant part using techniques known in the art. For instance, the mass of irradiated ultrahigh molecular weight polyethylene can be machined to produce the acetabular cup, the insert or liner of the acetabular cup, and trunnion bearings (e.g., between the modular head and the stem) of artificial hip joints, the tibial plateau, patellar button (patello-femoral articulation), and trunnion or other bearing components of artificial knee joints, the talar surface (tibiotalar articulation) and other bearing components of artificial ankle joints, the radio-numeral joint, ulno-humeral joint, and other bearing components of artificial elbow joints, the glenoro-humeral articulation and other bearing components of artificial shoulder joints, intervertebral disk replacements and facet joint replacements for the spine, temporo-mandibular joints (jaw), and finger joints.

After the residual non-polar solvent has been removed from the mass of irradiated ultrahigh molecular weight polyethylene and the mass has been formed into a medical implant or medical implant part, the resulting medical implant or medical implant part can be packaged in any suitable packaging material. Because a substantial portion of the free radicals present in the ultrahigh molecular weight polyethylene have been quenched, the medical implant or medical implant part is relatively stable to atmospheric oxidation. Accordingly, it is not necessary to package the medical implant or medical implant part in an inert atmosphere. Therefore, the medical implant or medical implant part can be packaged in an air-impermeable or air-permeable packaging material.

The medical implant or medical implant part can be sterilized using any suitable technique, desirably after packaging in a suitable material. Preferably, the packaged medical implant or packaged medical implant part is sterilized using a non-irradiative method so as to avoid the formation of additional free radicals in the ultrahigh molecular weight polyethylene. Suitable non-irradiative sterilization techniques include, but are not limited to, gas plasma or ethylene oxide methods known in the art. For example, the packaged medical implant or packaged medical implant part can be sterilized using a PlazLyte® Sterilization System (Abtox, Inc., Mundelein, Ill.).

EXAMPLE

This example further illustrates the invention but, of course, should not be construed as in any way limiting its scope. This example demonstrates the free radical quench process of the invention. Eight similar samples (Samples 1–8) of GUR 1050 ram extruded ultrahigh molecular weight polyethylene, which has a molecular weight of about 5,000,000 to about 6,000,000 atomic mass units, were provided in a prism shape, each side of which measured approximately 1 cm in length. The ultrahigh molecular weight polyethylene samples were then exposed to about 5 Mrad (50 KGy) of gamma radiation to cross-link at least a portion of ultrahigh molecular weight polyethylene contained therein.

Next, Samples 3–8 were completely immersed in six different solvents (decane, cineole, squalane, squalene, o-xylene, and decalin, respectively) at a temperature and for a time sufficient to quench at least a portion of the free radicals produced during the irradiation of the ultrahigh molecular weight polyethylene. The particular solvent, temperature, and time for each of the samples are set forth in the Table below. The samples were then dried under vacuum to remove any residual solvent. In particular, Samples 3–8 were dried under vacuum at a temperature of about 80° C. for about 8 hours. In order to ascertain the effects of the elevated drying temperature, Sample 2, which was not immersed in a solvent to quench the free radicals contained in the ultrahigh molecular weight polyethylene, was heated to a temperature of about 80° C. for about 8 hours.

Lastly, a core (measuring approximately 4 mm in diameter) was extracted from the approximate center of each of the samples (Samples 1–8). The relative free radical concentration present in each core was then measured using electron paramagnetic resonance (EPR) on an EMX-6/1 X-Band Spectrometer coupled with a high-sensitvity cavity (both available from Bruker BioSpin Corporation, Billerica, Mass.). An EPR spectrum for each of the samples was obtained by fixing the microwave frequency at the resonance frequency of the spectrometer's high-sensitivity sample chamber (the exact resonance frequency was determined before each test using the spectrometer, but the frequency typically was about 9.8 GHz) and scanning the magnetic field. At the aforementioned microwave frequency, the signal corresponding to the free radicals present in the ultrahigh molecular weight polyethylene appeared at about 3,480 to about 3,510 Gauss. The maximum peak-to-trough height for the signal observed in the aforementioned magnetic field range was then determined for each of the samples and is set forth in the Table below. While this measurement does not yield an absolute free radical concentration for the samples, the peak-to-trough height is directly proportional to the concentration of free radicals present in a given material and, therefore, can be used to compare the relative free radical concentration among a set of similar samples.

TABLE

Solvent, Quench Temperature, Quench Time, and EPR Signal for Samples 1–7.

| Sample | Quench Solvent | Quench Temperature (° C.) | Quench Time (minutes) | EPR Signal |
|---|---|---|---|---|
| 1 | — | — | — | 1,326,812 |
| 2 | — | 80 | 480 | 47,738 |
| 3 | Decane | 110 | 1440 | 532 |
| 4 | Cineole | 110 | 1440 | 1075 |
| 5 | Squalane | 110 | 1440 | 2412 |
| 6 | Squalene | 110 | 1440 | 19,670 |
| 7 | o-Xylene | 110 | 1440 | 821 |
| 8 | Decalin | 110 | 1440 | 2,411 |

As evidenced by the data set forth in the above Table, the free radical quench process of the invention results in a substantial decrease in the relative concentration of free radicals present in the ultrahigh molecular weight polyethylene. In particular, as is apparent from the data for Sample 1, irradiated ultrahigh molecular weight polyethylene which has not been subjected to any free radical quench process exhibited an EPR signal of about 1,326,812. While a specific value is provided for the EPR signal exhibited by Sample 1, it should be understood that the relatively high signal exhibited by Sample 1 approached the upper limits of the range in which the high-sensitivity spectrometer could reliably measure unpaired electron and free radical concentration. Accordingly, the value provided for Sample 1 should merely be considered an estimate of the relative free radical concentration of the sample generated for comparison purposes using the same measurement technique used to measure the relative free radical concentration of the remaining samples. As evidenced by the data for Sample 2, irradiated ultrahigh molecular weight polyethylene which was heated to simulate the drying conditions used for Samples 3-8, but was not subjected to the free radical quench process of the invention, exhibited an EPR signal of about 47,738. By way of contrast, each of the samples subjected to the process of the invention exhibited an EPR signal of less than 20,000, and many of the samples exhibited an EPR signal of less than 2,500. Indeed, a signal of less than about 1,500 is considered to by virtually indistinguishable from the background noise of the spectrum, and simple machining of the ultrahigh molecular weight polyethylene can produce an EPR of signal of about 300–700. The data set forth in the Table further demonstrates that, at the same quench temperature and quench time, the identity of the solvent impacts the amount of free radicals quenched by the process. For example, quenching Sample 5 with squalane for about 24 hours at a temperature of about 110° C. resulted in an EPR signal of approximately 2,412, while quenching Sample 6 with squalene for the same amount of time and at the same temperature resulted in an EPR signal of approximately 19,670. These results indicate that the process of the invention can be used to quench a substantial portion of the free radicals present in a sample of irradiated ultrahigh molecular weight polyethylene.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A process for quenching free radicals present in irradiated ultrahigh molecular weight polyethylene comprising the steps of:
   (a) providing a mass of irradiated ultrahigh molecular weight polyethylene, wherein the ultrahigh molecular weight polyethylene has a weight average molecular weight of about 400,000 atomic mass units or more, and the mass comprises free radicals,
   (b) immersing at least a portion of the mass of irradiated ultrahigh molecular weight polyethylene in a lipid having a temperature for a time and under conditions sufficient to quench a substantial portion of the free radicals contained therein, wherein the temperature of the lipid is maintained below the melting point of the ultrahigh molecular weight polyethylene,
   (c) removing the mass of irradiated ultrahigh molecular weight polyethylene from the lipid, and
   (d) removing lipid from the mass of irradiated ultrahigh molecular weight polyethylene.

2. The process of claim 1, wherein the ultrahigh molecular weight polyethylene has a molecular weight of about 1,000,000 atomic mass units or more.

3. The process of claim 1, wherein the lipid is a non-polar biocompatible lipid.

4. The process of claim 3, wherein the non-polar biocompatible lipid is removed from the mass of irradiated ultrahigh molecular weight polyethylene by exposing the mass to a reduced pressure atmosphere.

5. The process of claim 3, wherein the non-polar biocompatible lipid is selected from the group consisting of fatty acids, triglycerides, polyisoprenoids, cholesterol esters, and mixtures thereof.

6. The process of claim 3, wherein the non-polar biocompatible lipid is selected from the group consisting of glycerides, cholesterol, tocopherol esters, and mixtures thereof.

7. The process of claim 1, wherein the temperature of the lipid is maintained between about 100 and about 130° C.

8. The process of claim 7, wherein the temperature of the lipid is maintained between about 100 and about 120° C.

9. The process of claim 1, wherein the mass of irradiated ultrahigh molecular weight polyethylene is immersed in the lipid for about 2 hours or more.

10. The process of claim 9, wherein the mass of irradiated ultrahigh molecular weight polyethylene is immersed in the lipid for about 3 hours or more.

11. The process of claim 1, wherein about 90 percent or more of the free radicals present in the immersed portion of the mass of irradiated ultrahigh molecular weight polyethylene are quenched.

12. The process of claim 11, wherein about 95 percent or more of the free radicals present in the immersed portion of the mass of irradiated ultrahigh molecular weight polyethylene are quenched.

13. The process of claim 12, wherein about 98 percent or more of the free radicals present in the inirnersed portion of the mass of irradiated ultrahigh molecular weight polyethylene are quenched.

14. The process of claim 1, wherein the mass of irradiated ultrahigh molecular weight polyethylene is formed into a medical implant or medical implant part after the completion of step (d).

15. The process of claim 14, wherein the medical implant or medical implant part is packaged in an air-impermeable or air-permeable packaging material.

16. The process of claim 15, wherein the packaged medical implant or packaged medical implant part is sterilized using a non-irradiative method.

17. The process of claim 16, wherein the packaged medical implant or packaged medical implant part is sterilized using gas plasma or ethylene oxide.

18. The process of claim 1, wherein the mass of irradiated ultrahigh molecular weight polyethylene comprises a medical implant or a medical implant part.

19. The process of claim 18, wherein the medical implant or medical implant part is packaged in an air-impermeable or air-permeable packaging material after the completion of step (d).

20. The process of claim 19, wherein the packaged medical implant or packaged medical implant part is sterilized using a non-irradiative method.

21. The process of claim 1, wherein in step (d), substantially all of the lipid is removed from the mass of irradiated ultrahigh molecular weight polyethylene.

22. A process for quenching free radicals present in irradiated ultrahigh molecular weight polyethylene comprising the steps of:

(a) providing a mass of irradiated ultrahigh molecular weight polyethylene, wherein the ultrahigh molecular weight polyethylene has a weight average molecular weight of about 400,000 atomic mass units or more, and the mass comprises free radicals, (b) immersing at least a portion of the mass of irradiated ultrahigh molecular weight polyethylene in a non-polar solvent having a temperature for a time and under conditions sufficient to quench a substantial portion of the free radicals contained therein, wherein the temperature of the non-polar solvent is maintained below the melting point of the ultrahigh molecular weight polyethylene, (c) removing the mass of irradiated ultrahigh molecular weight polyethylene from the non-polar solvent, and (d) removing non-polar solvent from the mass of irradiated ultrahigh molecular weight polyethylene;

wherein the non-polar solvent is a non-polar low molecular weight solvent selected from the group consisting of heptane, octane, nonane, decane, decalin, octanol, cineole, and mixtures thereof.

* * * * *